(12) United States Patent
Brandt et al.

(10) Patent No.: US 8,998,868 B2
(45) Date of Patent: Apr. 7, 2015

(54) OSTOMY BAG WITH A COMPACTED SHEATH

(75) Inventors: Joergen-Ulrik Brandt, Bogense (DK); Tina Joergensen, Bogense (DK)

(73) Assignee: Stoma Guard ApS, Lunderskov (DK)

( * ) Notice: Subject to any disclaimer, the term of this patent is extended or adjusted under 35 U.S.C. 154(b) by 98 days.

(21) Appl. No.: 13/638,387

(22) PCT Filed: Apr. 1, 2011

(86) PCT No.: PCT/DK2011/050108
§ 371 (c)(1),
(2), (4) Date: Dec. 26, 2012

(87) PCT Pub. No.: WO2011/124225
PCT Pub. Date: Oct. 13, 2011

(65) Prior Publication Data
US 2013/0144236 A1 Jun. 6, 2013

(30) Foreign Application Priority Data

Apr. 7, 2010 (DK) .................................. 2010 00289

(51) Int. Cl.
*A61F 5/44* (2006.01)
*A61F 5/448* (2006.01)
*A61F 5/445* (2006.01)
*A61F 5/443* (2006.01)

(52) U.S. Cl.
CPC .................. *A61F 5/448* (2013.01); *A61F 5/445* (2013.01); *A61F 5/443* (2013.01)

(58) Field of Classification Search
CPC ........... A61F 5/44; A61F 5/445; A61F 5/448; A61F 5/443; A61F 2005/44; A61F 2005/4402; A61F 2005/445

USPC .......................... 604/344, 339, 342, 343, 341
See application file for complete search history.

(56) References Cited

U.S. PATENT DOCUMENTS

| | | | | | |
|---|---|---|---|---|---|
| 3,089,493 | A | * | 5/1963 | Galindo | 604/342 |
| 4,256,110 | A | * | 3/1981 | Scoville | 604/342 |
| 4,917,690 | A | * | 4/1990 | Hunger | 604/338 |
| 5,423,782 | A | * | 6/1995 | Wolrich | 604/339 |

(Continued)

FOREIGN PATENT DOCUMENTS

| | | |
|---|---|---|
| EP | 2 108 344 | 10/2009 |
| WO | WO 2005/082272 | 9/2005 |

OTHER PUBLICATIONS

International Search Report for International Application No. PCT/DK2011/050108 mailed Jun. 20, 2011.

*Primary Examiner* — Leslie Deak
*Assistant Examiner* — Kai Weng
(74) *Attorney, Agent, or Firm* — Merchant & Gould P.C.

(57) ABSTRACT

There is provided a disposable ostomy bag assembly (1) comprising a bag (3) for receiving bodily waste materials; a compactable sheath (2) for closing and sealing the bag (3) after use; and a flange (4) for securing the assembly to the body of a patent and provided with an orifice to enable bodily waste to be received by the bag (3). The ostomy assembly (1) solves the problem of escaping malodour and bodily waste when the patient detaches the ostomy bag from the body (face plate (5)). The compactable sheath (2) can be stretched to acquire a cylindrical sheath (2) extending from the flange (4), whereby the sheath (2) may be closed in order to seal the contents of the bag (3). Closing the sheath (2) may simply be done by tying a knot (6).

10 Claims, 3 Drawing Sheets

(56) References Cited

U.S. PATENT DOCUMENTS

| | | |
|---|---|---|
| 5,938,647 A | 8/1999 | Smith |
| 6,709,422 B2 * | 3/2004 | Hessel et al. ................ 604/342 |
| 7,374,626 B2 * | 5/2008 | Van Der Leden ............ 156/73.1 |
| 2002/0082570 A1 * | 6/2002 | Mishima et al. .............. 604/332 |
| 2003/0023210 A1 | 1/2003 | Bedard et al. |
| 2003/0073962 A1 | 4/2003 | Olsen et al. |
| 2006/0206069 A1 * | 9/2006 | Cline ........................... 604/337 |
| 2007/0260206 A1 * | 11/2007 | Mullejans et al. ............ 604/332 |

* cited by examiner

OSTOMY BAG WITH A COMPACTED SHEATH

This application is a National Stage Application of PCT/DK2011/050108, filed 1 Apr. 2011, which claims benefit of Serial No. PA 2010 00289, filed 7 Apr. 2010 in Denmark and which applications are incorporated herein by reference. To the extent appropriate, a claim of priority is made to each of the above disclosed applications.

FIELD OF THE INVENTION

The present invention relates to a disposable ostomy bag assembly with a bag for receiving bodily waste materials. More specifically the present invention relates to an ostomy bag assembly provided with a compacted sheath for closing and sealing the bag after use.

BACKGROUND OF THE INVENTION

Following surgery, patients who have had a surgical construction of an artificial excretory opening such as ileostomy or colostomy patients use ileostomy/colostomy bags (collectively referred to as ostomy bags) to collect bodily waste materials. These bodily waste materials include gases, liquids and solids. The waste material may be semi-solid faecal waste. It is desirable in any event to dispose the collected materials with minimal handling from the user. It is also desirable to avoid undesired smell to escape from the ostomy bag when it is detached from the patient after use and before being disposed.

Some bags are intended for multiple use purposes and generally the surgical patients find that they have to empty the collection bag many times during the day. A given collection bag is thus fitted with waste discharge outlet through which the waste materials collected from the artificial excretory opening can be discharged. It is not unusual to empty these bags between six and ten times in any given day. A collection bag will typically be worn for a number of consecutive days before being replaced with a new bag. Given the nature of the materials which they collect, such collection bags are generally made of plastics materials.

One commercial toilet flushable pouch (similar to the device described in U.S. Pat. No. 5,938,647) is available from Welland Medical Limited in the UK. Their product is an inner liner pouch which is designed to fit within the bag worn by the user. The pouch is designed and arranged to collect the bodily waste materials and provide a barrier between those materials and the bag. None of the bodily waste materials therefore comes into direct contact with the inner of the bag. Additionally, the bodily waste materials can be removed by removing the inner pouch without contamination of the bag. This means however that the inner pouch must be of a relatively complex design as it must be adapted to fit to the artificial opening of the body in the same way as the collection bag. This is necessary in order to avoid contamination of the collection bag with bodily waste material.

U.S.2003023210A1 discloses an ostomy pouch and an insert defining an interior volume. The insert is configured for positioning within the ostomy pouch and can define a pair of handles, a pair of pleated side panels, or a pair of handles and a pair of pleated side panels.

WO05082272A2 discloses an ostomy appliance comprising a receiving member and a disposable bag liner. Furthermore WO05082272A2 discloses a bag being compacted lengthwise while twisting a bottom part in relation to a rim and a method of compacting the same.

Various disposable ostomy bags have been disclosed in the prior art. Meanwhile, none of these are equipped with means for simple closing and sealing the contents of the bags before disposal. Moreover, the prior art does not disclose an ostomy bag equipped with means for simple closing and sealing of the contents of the bag and which means can maintain the seal after the bag has been detached from the body of the patient thereby reducing the risk of escaping odour or soiling of the clothing by dripping output from the stoma.

In general the containers and methods of disposal of the prior art are not convenient for the end user and are generally difficult to carry around.

The inventors have now devised improvements to such disposal receptacles.

SUMMARY OF THE INVENTION

The present invention describes a disposable ostomy bag assembly which solves the problems discussed above. Specifically there is provided a disposable ostomy bag assembly comprising:
a bag for receiving bodily waste materials;
a compactable sheath for closing and sealing the bag after use; and
a flange for securing the assembly to the body of a patient and provided with an orifice to enable bodily waste to be received by the bag;
wherein said bag and sheath are secured to said flange.

The ostomy assembly of the present invention solves the problem of escaping malodour and bodily waste when the patient detaches the ostomy bag from the body (face plate). The compactable sheath can be stretched to acquire a cylindrical sheath extending from the flange, whereby the sheath may be closed in order to seal the contents of the bag. Closing the sheath may simply be done by tying a knot.

In a preferred embodiment of the present invention the bag and sheath are welded to the flange. Alternatively the sheath is glued to said flange either alone or together with the bag.

In a particularly preferred embodiment the sheath is made from a plastic film, which renders the sheath particularly easy to close by tying a knot. The sheath may also be provided with an adhesive layer on its inside so that pressing the sheath together makes a seal.

The sheath may be made from plastic film and in particularly materials conventionally used for the preparation of ostomy appliances. Such materials are suitably films composed of any suitable material, which is heat sealable and sufficiently impervious for unpleasant odours such as polyolefin films or combinations of such films, e.g. polyethylene or a co-extrudate of polyethylene and polyvinylidene chloride. Preferably the plastic film is selected from the group consisting of: polyethylene, polyethylene terephthalate, polypropylene, and polyvinylinene chloride.

In a particularly preferred embodiment of the present invention the sheath is provided with folding lines for easy compacting the sheath lengthwise. The sheath may be secured on either the front side (facing the body) or back-side of the flange to be attached to the body of the patient. For practical reasons the sheath is preferably secured on the bag-side of the flange.

DETAILED DESCRIPTION OF THE INVENTION

The present invention solves the problems discussed above in prior art ostomy bags by providing an integrating closing mechanism for sealing the contents of the bag with a compactable sheath.

The inventive ostomy bag assembly contributes to improved patient comfort and easy handling of used disposable ostomy bags.

Figure 1:
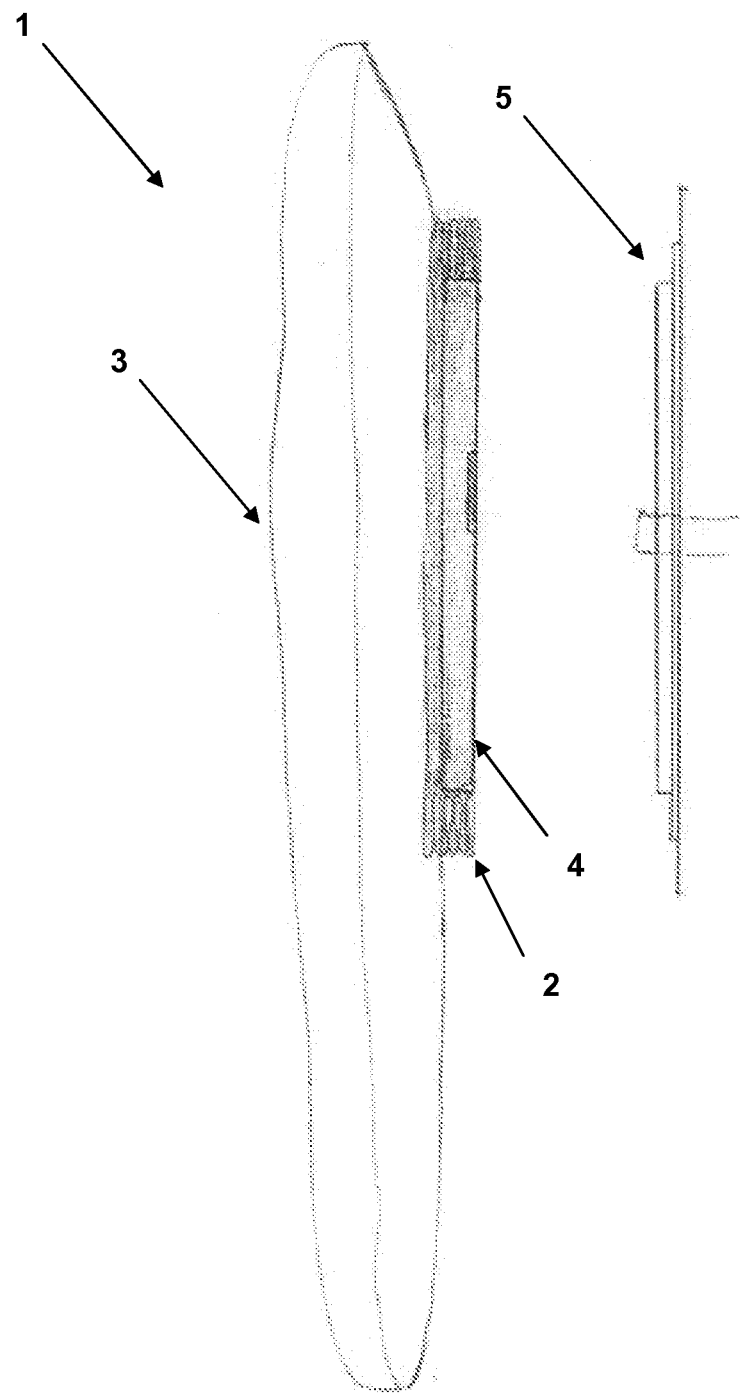
FIG. 1 shows a side view of the ostomy bag assembly of the present invention, wherein the sheath is its compacted position.

Reference is made to FIG. 1, which shows a side view of the ostomy bag assembly (1) of the present invention, wherein the sheath (2) is in its compacted position. In addition to the compactable sheath (2) the ostomy bag assembly (1) includes a bag (3) for receiving bodily waste materials; and a flange (4) for securing the assembly to the face plate (5) on the body of a patient. This ostomy assembly solves the problem of escaping malodour and bodily waste when the patient detaches the ostomy bag (3) from the face plate (5). The compactable sheath (2) can be stretched to acquire a cylindrical sheath extending from the flange, whereby the sheath may be closed in order to seal the contents of the bag (see FIG. 2).

Figure 2:
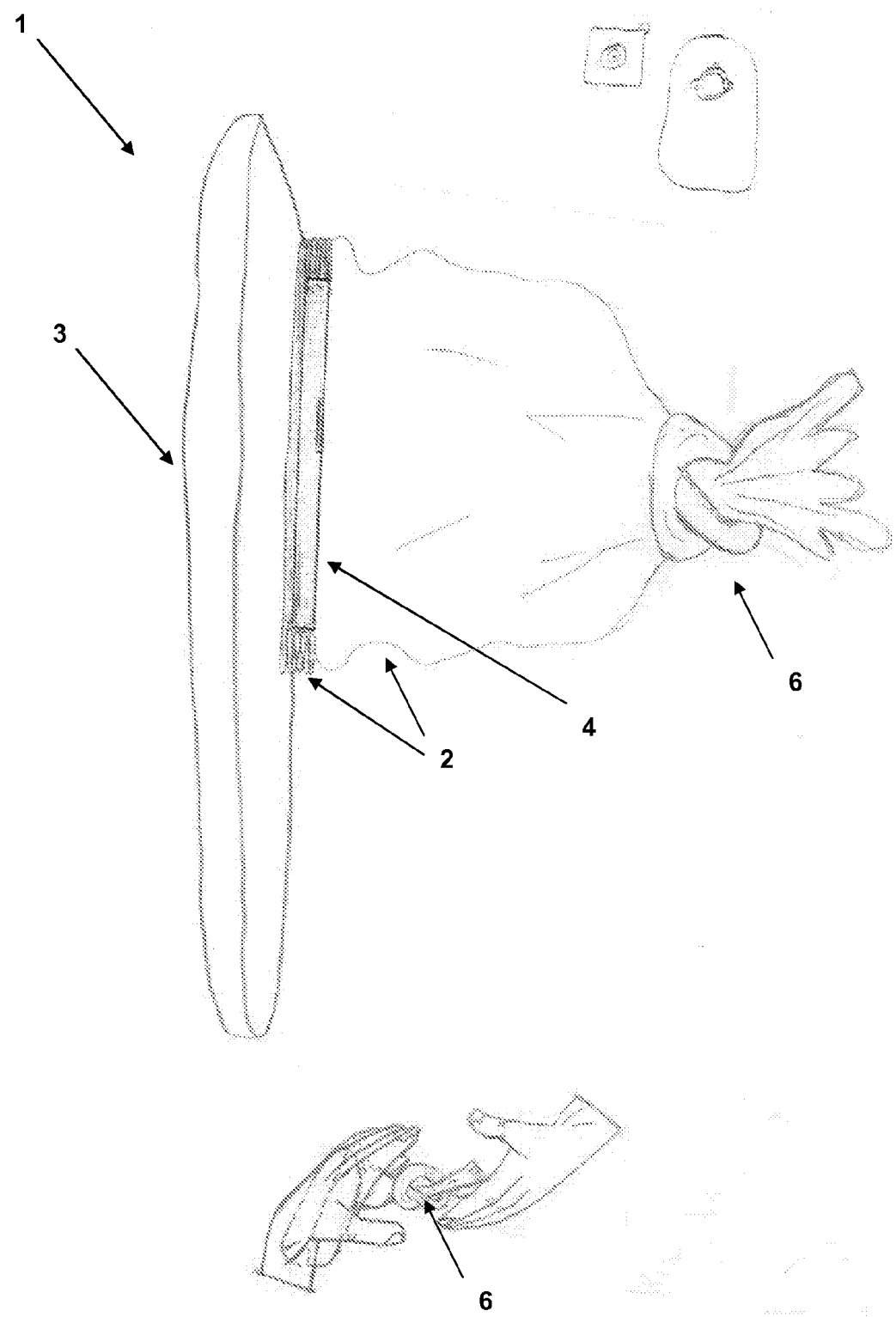
FIG. 2 shows a view of the ostomy bag assembly of the present invention, wherein the sheath is stretched and tied in a knot in order to seal the contents of the bag.

Reference is made to FIG. 2 showing a side view of the ostomy bag assembly (1) of the present invention, wherein the sheath (2) is stretched and tied in a knot (6) in order to seal the contents of the bag. This solves the problem of escaping malodour and bodily waste when the patient detaches the ostomy bag (3) from the face plate (5). FIG. 2 also shows the flange (4) for securing the assembly to the face plate (5) on the body of a patient.

Figure 3:
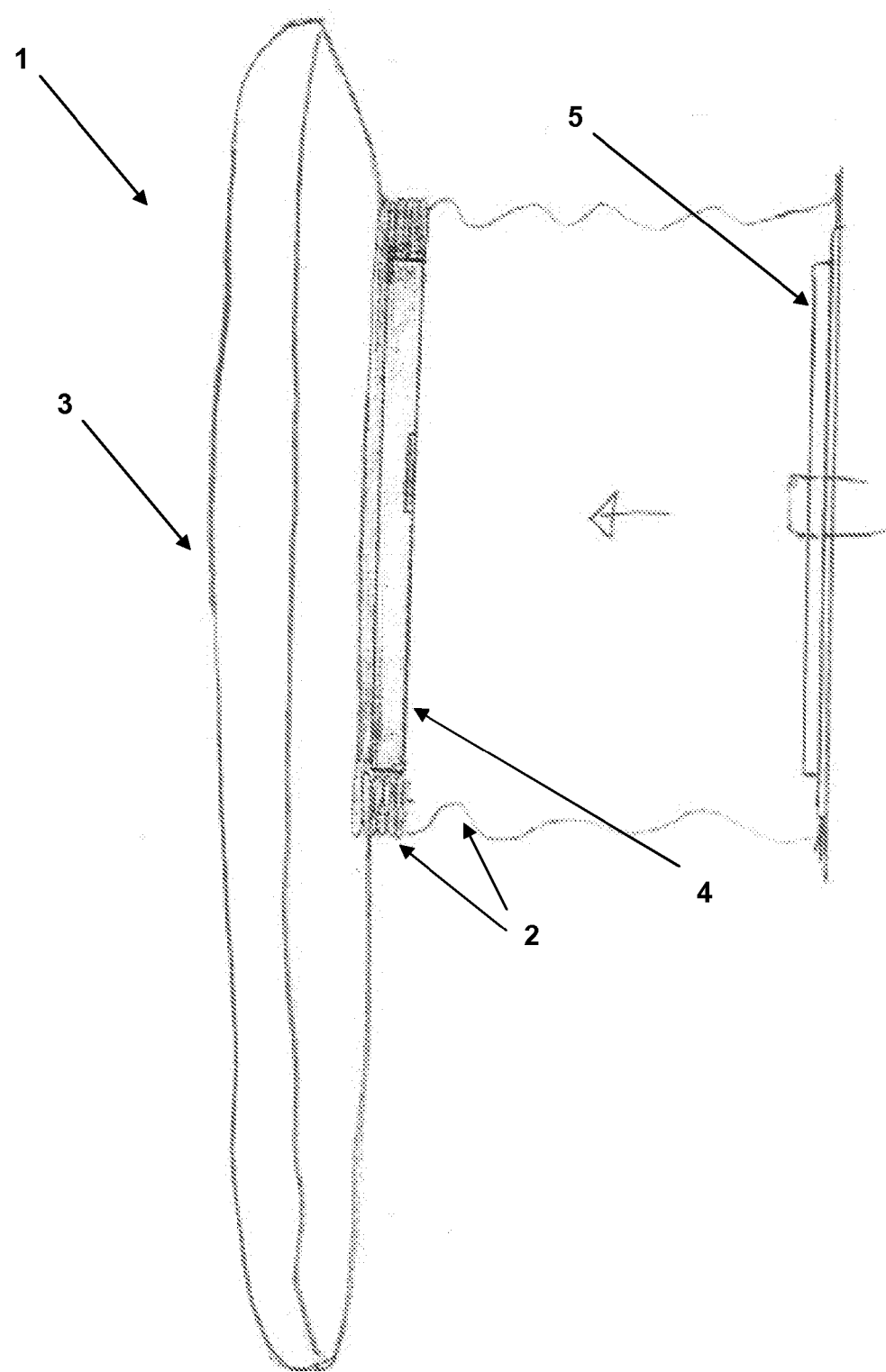
FIG. 3 shows a view of the ostomy bag assembly of the present invention, wherein the sheath is stretched and adheres to the face place on the body of the patient.

Reference is made to FIG. 3 also showing a side view of the ostomy bag assembly (1), wherein the sheath (2) is stretched and adheres to the face place (5) on the body of the patient. In order to ensure adherence of the sheath (2) to the face plate (5) the sheath (2) is provided (in this embodiment) with an adhesive layer. The figure also shows the flange (4) for securing the assembly to the face plate (5) on the body of a patient. Alternatively, the sheath (2) is provided with a rim or similar structure that can be affixed to the face plate (5). In this way the patient may detach the bag (3) from the face plate (5) without any malodour leaves the bag (3) until the patient detaches the sheath (2) from the face plate (5) before closing the sheath (2) and thereby sealing the contents of the bag (3). This manoeuvre may be done quickly so that only a minute amount of malodour leaves the bag.

The invention claimed is:

1. A disposable ostomy bag assembly comprising:
   a bag for receiving bodily waste materials, the bag having an outside;
   a compactable sheath adapted for closing and sealing the bag after use, the compactable sheath having a first end and a second end; and
   a flange for securing the assembly to a face-plate positioned on the body of a patient and provided with an orifice to enable bodily waste to be received by the bag, the flange having an outer perimeter;
   wherein said bag and the first end of the sheath are jointly secured to said flange, said compactable sheath extending around an outer perimeter of the flange, and wherein the sheath is constructed to extend from the outside of the bag at the sheath first end to the face plate at the sheath second end, wherein the second end of the sheath is constructed for connecting to the face plate.

2. The disposable ostomy bag assembly of claim 1, wherein said bag and sheath are welded to said flange.

3. The disposable ostomy bag assembly of claim 1, wherein said sheath is glued to said flange.

4. The disposable ostomy bag assembly of claim 1, wherein said sheath is made from a plastic film.

5. The disposable ostomy bag assembly of claim 4, wherein the plastic film is selected from the group consisting of: polyethylene, polyethylene terephthalate, polypropylene, and polyvinylinene chloride.

6. The disposable ostomy bag assembly of claim 1, wherein said sheath is provided with folding lines for compacting the sheath lengthwise.

7. The disposable ostomy bag assembly of claim 1, wherein said sheath is secured on the bag-side of the flange.

8. The disposable ostomy bag assembly of claim 1, wherein said sheath comprises an attachment mechanism for attaching the sheath to a face-plate positioned on the patient.

9. The disposable ostomy bag assembly of claim 8, wherein the attachment to the body of a patient is an adhesive layer on the surface of the sheath oriented towards the patient.

10. The disposable ostomy bag assembly of claim 1, wherein the sheath extends continuously from the first end to the second end.

* * * * *